United States Patent
DeCarlo

(10) Patent No.: US 9,057,468 B2
(45) Date of Patent: Jun. 16, 2015

(54) WEDGE COUPLING

(75) Inventor: Arnold V. DeCarlo, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1646 days.

(21) Appl. No.: 12/271,109

(22) Filed: Nov. 14, 2008

(65) Prior Publication Data

US 2009/0138010 A1    May 28, 2009

Related U.S. Application Data

(60) Provisional application No. 60/990,542, filed on Nov. 27, 2007.

(51) Int. Cl.
*F16L 37/56* (2006.01)
*F16L 37/098* (2006.01)
*A61B 18/14* (2006.01)
*A61M 39/12* (2006.01)
*A61M 39/10* (2006.01)
*A61B 18/00* (2006.01)
*A61B 18/02* (2006.01)

(52) U.S. Cl.
CPC .............. *F16L 37/098* (2013.01); *A61M 39/12* (2013.01); *A61M 39/105* (2013.01); *A61M 2039/1027* (2013.01); *A61B 18/14* (2013.01); *A61B 2018/00178* (2013.01); *A61B 2018/0231* (2013.01); *F16L 37/56* (2013.01)

(58) Field of Classification Search
CPC .................. F16L 37/56; F16L 37/098; A61B 2018/00172; A61B 2018/00178; A61M 39/105; A61M 39/12; A61M 2039/1027
USPC ............. 606/41; 604/103, 533–536; 285/246, 285/255, 256, 319
See application file for complete search history.

(56) References Cited

U.S. PATENT DOCUMENTS

| | | | |
|---|---|---|---|
| 1,911,229 A | | 5/1933 | Gleim |
| 2,874,981 A | * | 2/1959 | Sherwood ................... 285/238 |
| 3,189,370 A | * | 6/1965 | Marshail ........................ 285/27 |
| 3,195,933 A | * | 7/1965 | Jacobs .......................... 285/247 |
| 3,631,363 A | | 12/1971 | Miller |
| 3,942,528 A | | 3/1976 | Loeser |
| 4,253,686 A | * | 3/1981 | Aitken et al. ................. 285/249 |
| 4,397,313 A | | 8/1983 | Vaguine |
| 4,435,174 A | | 3/1984 | Redmond et al. |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Nathan R Price

(57) ABSTRACT

A wedge coupling for coupling a tubing to a housing is disclosed. The wedge coupling includes a base having an opening defined therein and configured to receive a portion of the tubing therethrough and a plurality of prongs disposed on the base and around an inner periphery of the opening. The plurality of prongs are configured to slidably engage the housing and to deflect inwardly to secure the tubing to a nozzle adapter disposed within the housing.

8 Claims, 6 Drawing Sheets

(56) References Cited

U.S. PATENT DOCUMENTS

| | | | |
|---|---|---|---|
| D273,993 S | 5/1984 | Schulte et al. | |
| 4,462,412 A | 7/1984 | Turner | |
| 4,508,374 A * | 4/1985 | Kantor | 285/319 |
| 4,572,190 A | 2/1986 | Azam et al. | |
| 4,645,492 A | 2/1987 | Weeks | |
| 4,798,215 A | 1/1989 | Turner | |
| 4,802,864 A | 2/1989 | Michaels et al. | |
| 5,097,844 A | 3/1992 | Turner | |
| D350,201 S | 8/1994 | Hirsch et al. | |
| 5,354,282 A | 10/1994 | Bierman | |
| 5,388,873 A * | 2/1995 | Enayati | 285/256 |
| 5,417,210 A | 5/1995 | Funda et al. | |
| 5,456,671 A | 10/1995 | Bierman | |
| 5,578,013 A | 11/1996 | Bierman | |
| 5,640,476 A | 6/1997 | Womack et al. | |
| 5,672,847 A | 9/1997 | Piatt | |
| 5,690,616 A | 11/1997 | Mogg | |
| 5,702,371 A | 12/1997 | Bierman | |
| 5,710,851 A | 1/1998 | Walter et al. | |
| 5,860,952 A | 1/1999 | Quinn | |
| 5,890,926 A | 4/1999 | Pauza et al. | |
| 5,910,128 A | 6/1999 | Quinn | |
| 5,916,199 A | 6/1999 | Miles | |
| 5,947,931 A | 9/1999 | Bierman | |
| 6,001,081 A | 12/1999 | Collen | |
| 6,013,875 A | 1/2000 | Fridenberg et al. | |
| 6,031,375 A | 2/2000 | Atalar et al. | |
| 6,036,673 A | 3/2000 | Quinn | |
| 6,159,198 A | 12/2000 | Gardeski et al. | |
| 6,375,606 B1 | 4/2002 | Garibaldi et al. | |
| 6,427,953 B1 | 8/2002 | Dickens | |
| 6,428,515 B1 | 8/2002 | Bierman et al. | |
| 6,477,770 B1 | 11/2002 | Dickens | |
| 6,544,247 B1 | 4/2003 | Gardeski et al. | |
| 6,554,489 B2 | 4/2003 | Kent et al. | |
| 6,603,994 B2 | 8/2003 | Wallace et al. | |
| 6,634,801 B1 | 10/2003 | Waldron et al. | |
| 6,695,490 B2 | 2/2004 | Shirakawa et al. | |
| 6,725,080 B2 | 4/2004 | Melkent et al. | |
| 6,808,315 B2 | 10/2004 | Asada | |
| 6,817,780 B2 | 11/2004 | Ngo | |
| 6,878,136 B2 | 4/2005 | Fleury et al. | |
| 6,918,894 B2 | 7/2005 | Fleury et al. | |
| 6,932,515 B2 | 8/2005 | Ngo | |
| D525,359 S | 7/2006 | Stephens | |
| 7,198,066 B2 | 4/2007 | Kagenow | |
| D543,277 S | 5/2007 | White | |
| 7,229,051 B2 | 6/2007 | Mailhot, Jr. | |
| 7,270,351 B2 * | 9/2007 | Chelchowski et al. | 285/382.7 |
| 7,312,407 B2 | 12/2007 | Case | |
| 7,354,421 B2 | 4/2008 | Bierman | |
| 7,439,736 B2 | 10/2008 | Meaney et al. | |
| 7,467,015 B2 | 12/2008 | Van der Weide | |
| 7,565,207 B2 | 7/2009 | Turner et al. | |
| 2002/0022836 A1 | 2/2002 | Goble et al. | |
| 2004/0097805 A1 | 5/2004 | Verard et al. | |
| 2004/0195831 A1 * | 10/2004 | Ohya | 285/242 |
| 2004/0239110 A1 * | 12/2004 | Pedersen et al. | 285/255 |
| 2004/0242992 A1 | 12/2004 | Hareyama | |
| 2006/0264911 A1 * | 11/2006 | Nelson | 604/890.1 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |

(56) References Cited

FOREIGN PATENT DOCUMENTS

| WO | WO2004/112628 | 12/2004 |
|----|---------------|---------|
| WO | WO2005/016119 | 2/2005  |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw-Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion LocalizerUse with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi.et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael.Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Proitatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection Duiing Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.

(56) References Cited

OTHER PUBLICATIONS

Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite-Element Codes to Model Electrical Heating and Non-Linear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/US04/13273 dated Dec. 15, 2004.
International Search Report PCT/US04/15311 dated Jan. 12, 2004.

(56) References Cited

OTHER PUBLICATIONS

International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key:Visualize A Virtual Keyboard. One With No Moving Parts", 2004 Advanced Input Systems, located at: <http://www.advanced-input.com/lightkey>.

* cited by examiner

WEDGE COUPLING

CROSS-REFERENCE TO RELATED APPLICATIONS

This application claims the benefit of priority to U.S. Provisional Application Ser. No. 60/990,542 entitled "WEDGE COUPLING" filed Nov. 27, 2007 by Arnold V. DeCarlo, which is incorporated by reference herein.

BACKGROUND

1. Technical Field

The present disclosure relates generally to ablation systems. More particularly, the present disclosure is directed to a system and method for coupling a flexible conduit to ablation probes, liquid supplies, gas supplies, etc.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave or radiofrequency energy is used to coagulate and/or ablate tissue to denature or kill the cancerous cells. Energy is applied via ablation antenna probes which penetrate tissue to reach tumors. There are several types of ablation probes.

In certain procedures it is desirable to provide liquid to the ablation probe. The liquid may be used as a coolant to reduce the temperature at the tip of the probe in order to maintain the desired ablation temperature. In addition, the liquid may be used a dielectric to provide for dynamic matching of a microwave ablation probe. The liquid is usually provided to the probe via tubing.

SUMMARY

According to one aspect of the present disclosure a wedge coupling for coupling a tubing to a nozzle adapter within a housing is disclosed. The wedge coupling includes a base having an opening defined therein and configured to receive a portion of the tubing therethrough and a plurality of prongs disposed on the base and around an inner periphery of the opening. The plurality of prongs are configured to slidably engage the housing and to deflect inwardly to secure the tubing to a nozzle adapter disposed within the housing.

According to another aspect of the present disclosure an ablation probe is disclosed. The probe includes a housing having a funnel-shaped inner surface and a nozzle adapter connected thereto and a tubing configured to slide into the funnel-shaped inner surface and over the nozzle adapter. The probe also includes a wedge coupling having a base with an opening defined therein and configured to receive a portion of the tubing therethrough and a plurality of prongs disposed on the base and around an inner periphery of the opening. The plurality of prongs are configured to slidably engage the housing and to deflect inwardly to secure the tubing to a nozzle adapter disposed within the housing.

A method for securing a tubing to a housing is also contemplated by the present disclosure. The method includes the steps of inserting a tubing into a wedge coupling that includes a base having an opening defined therein and configured to receive a portion of the tubing therethrough. The coupling also includes a plurality of prongs disposed on the base and around an inner periphery of the opening. The method also includes the step of inserting the tubing with the wedge coupling disposed thereon into a housing having a funnel-shaped inner surface and a nozzle adapter connected thereto, such that the tubing slides into the funnel-shaped inner surface and over the nozzle adapter and the plurality of prongs slidably engage the housing and deflect inwardly thereby securing the tubing to the nozzle adapter.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
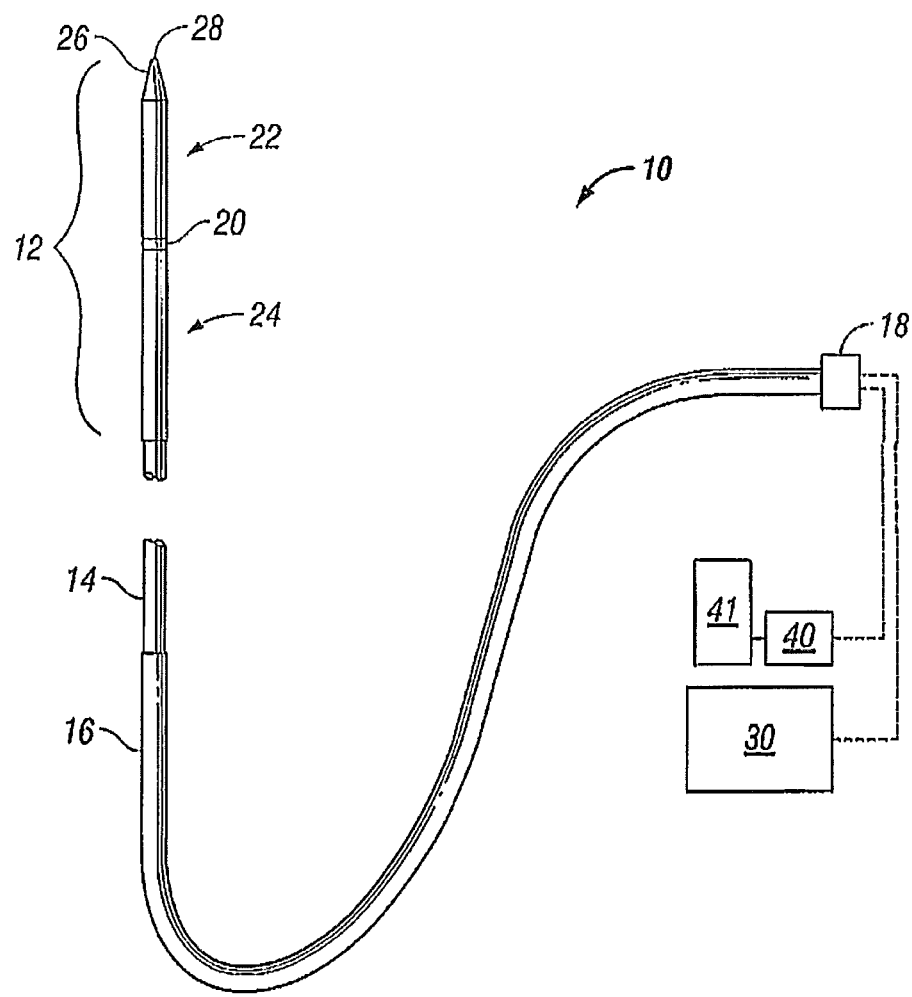
FIG. 1 is a schematic diagram of an ablation probe assembly according to the present disclosure.

The present disclosure provides for a system and method to couple various types of flexible tubing to input and/or output ports of various ablation apparatuses (e.g., a microwave probe, electrosurgical monopolar electrodes, pump, etc.). In particular, the tubing may be used in cooling systems which circulate cooling liquid through the microwave probe. FIG. 1 shows a diagram of an ablation probe assembly 10 which may be any type of probe suitable for depositing radiofrequency energy and may be used with a cooling system as described herein. The antenna assembly 10 is generally comprised of radiating portion 12 that may be coupled by feedline 14 (or shaft) via conduit 16 to connector 18, which may further connect the assembly 10 to a power generating source 30, e.g., a generator and a supply pump 40.

Assembly 10 includes a dipole ablation probe assembly. Other antenna assemblies, e.g., monopole or leaky wave antenna assemblies, may also be utilized. Distal portion 22 of radiating portion 12 may include a tapered end 26 that terminates at a tip 28 to allow for insertion into tissue with minimal resistance. In those cases where the radiating portion 12 is inserted into a pre-existing opening, tip 28 may be rounded or flat.

Proximal portion 24 is located proximally of distal portion 22, and junction member 20 is located between both portions such that a compressive force is applied by distal and proximal portions 22, 24 upon junction member 20. Placing distal and proximal portions 22, 24 in a pre-stressed condition prior to insertion into tissue enables assembly 10 to maintain a stiffness that is sufficient to allow for unaided insertion into the tissue while maintaining a minimal antenna diameter, as described in detail below.

Feedline 14 may electrically connect antenna assembly 10 via conduit 16 to generator 30 and usually includes a coaxial cable made of a conductive metal, which may be semi-rigid or flexible. Feedline 14 may also have a variable length from a proximal end of radiating portion 12 to a distal end of conduit 16 ranging between about 1 to 15 inches. The feedline 14 may be constructed of copper, gold, stainless steel or other conductive metals with similar conductivity values. The metals may also be plated with other materials, e.g., other conductive materials, to improve their properties, e.g., to improve conductivity or decrease energy loss, etc.

Figure 2:
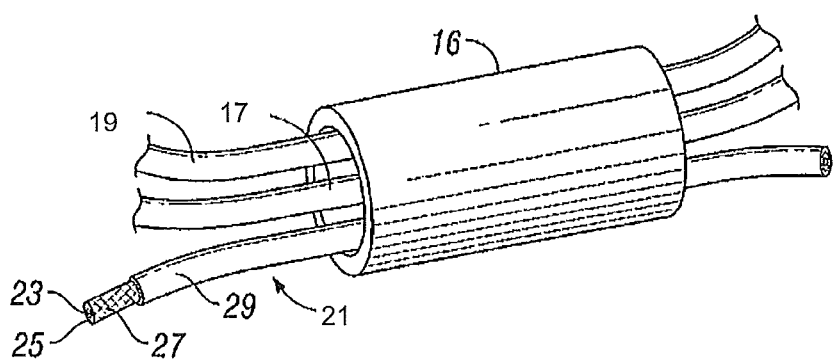
FIG. 2 is a perspective view of a conduit of the ablation probe assembly of FIG. 1.

As shown in FIG. 2, the conduit 16 includes a flexible coaxial cable 21 and one or more flexible tubes, inflow tubing 17 and outflow tubing 19 for supplying and withdrawing cooling liquid into and out of the radiating portion 12, respectively. The cable 21 includes an inner conductor 23 (e.g., wire) surrounded by an insulating spacer 25, which is concentrically disposed within an outer conductor 27 (e.g., cylindrical conducting sheath). The cable 21 may also include an outer insulating sheath 29 surrounding the outer conductor 27. The connector 18 couples the inflow and outflow tubing 17, 19 to the supply pump 40 and the cable 21 to the generator 30. The supply pump 40 is coupled to a supply tank 41 that stores the cooling liquid and maintains the liquid at a predetermined temperature. In one embodiment, the supply tank 41 may include a cooling unit that cools the returning cooling liquid from the outflow tubing 19.

The cooling fluid may be pumped using positive pressure through inflow tubing 17; alternatively, negative pressure may also be used to draw the fluid out of the region through outflow tubing 19. Negative pressure through outflow tubing 19 may be utilized either alone or in conjunction with positive pressure through inflow tubing 17. Alternatively, positive pressure through inflow tubing 17 may be utilized either alone or in conjunction with negative pressure through outflow tubing 19. In pumping the cooling fluid, the cooling fluid may be passed at a constant and uniform flow rate. In another variation, the flow may be intermittent such that a volume of cooling fluid may be pumped into the radiating portion 12 and allowed to warm up by absorbing heat from the antenna. Once the temperature of the fluid reaches a predetermined level below temperatures where thermal damage to tissue occurs, the warmed fluid may be removed and displaced by additional cooling fluids. Temperature sensors (such as thermistors, thermocouples, etc.) may be incorporated within or upon radiating portion 12 to sense the fluid and/or outer jacket temperatures. The system may be configured to automatically pump additional cooling fluid from the supply tank 41 once the sensed temperature reaches the predetermined level or it may be configured to notify the user via, e.g., an audible or visual alarm.

The cooling fluid used may vary depending upon desired cooling rates and the desired tissue impedance matching properties. Biocompatible fluids may be included which have sufficient specific heat values for absorbing heat generated by radio frequency ablation probes, e.g., liquids including, but not limited to, water, saline, liquid chlorodifluoromethane, etc. In another variation, gases (such as nitrous oxide, nitrogen, carbon dioxide, etc.) may also be utilized as the cooling fluid. For instance, an aperture within the radiating portion 12 may be configured to take advantage of the cooling effects from the Joule-Thompson effect, in which case a gas, e.g., nitrous oxide, may be passed through the aperture to expand and cool the radiating portion 12. In yet another variation, a combination of liquids and/or gases, as mentioned above, may be utilized as the cooling medium.

Figure 3:
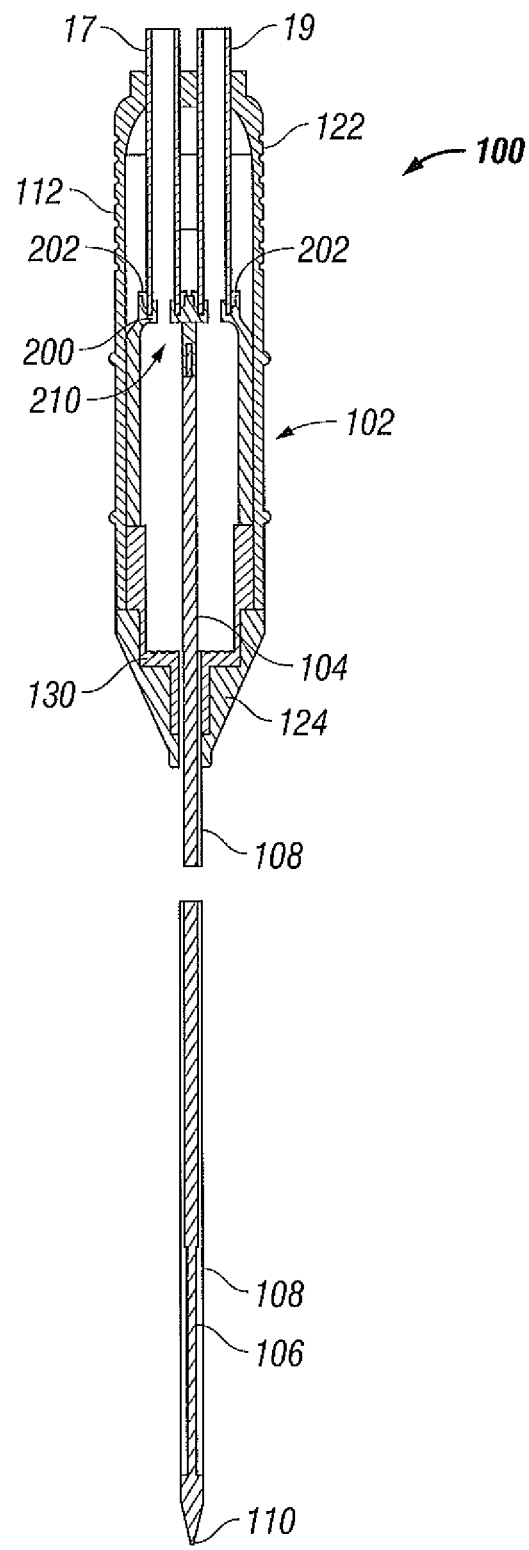
FIG. 3 are a cross-sectional view of an ablation probe cooling assembly according to one embodiment of the present disclosure.

FIG. 3 show a cross-sectional side view and an end view, respectively, of one variation of the antenna assembly to (e.g., antenna cooling assembly 100) that may be utilized with any number of conventional ablation probes or the ablation probes described herein, particularly the straight probe configuration as shown in FIG. 1. Although this variation illustrates the cooling of a straight probe antenna, a curved or looped ablation probe may also utilize much of the same or similar principles, as further described below.

Antenna cooling assembly 100 includes a cooling handle assembly 102 and an elongate outer jacket 108 extending from handle assembly 102. Outer jacket 108 may extend and terminate at tip 110, which may be tapered to a sharpened point to facilitate insertion into and manipulation within tissue, if necessary. Ablation probe 104 may be positioned within handle assembly 102 such that the radiating portion 106 of antenna 104 extends distally into outer jacket 108 towards tip 110. Inflow tubing 17 may extend into a proximal end of handle body 112 and distally into a portion of outer jacket 108. Inflow tubing 17 may also extend from within handle body 112 such that the distal ends of inflow tubing 17 and outflow tubing 19 are in fluid communication with one another, as described in further detail below.

As shown, handle body 112 may be comprised of proximal handle hub 122, which encloses a proximal end of antenna 104, and distal handle hub 124, which may extend distally into outer jacket 108. Proximal handle hub 122 and distal handle hub 124 may each be configured to physically interfit with one another at hub interface 130 to form a fluid tight seal. Accordingly, proximal handle hub 122 may be configured to be received and secured within a correspondingly configured distal handle hub 124 (seen in FIG. 3 as a male-female connection). Proximal and distal handle hubs 122, 124 may each be formed from the same, similar or different materials. If hubs 122, 124 are fabricated from the same material, a variety of non-conductive materials may be utilized, e.g., polymers, polyimides, plastics, etc. Alternatively, proximal handle hub 122 may be fabricated from a metal or alloy, e.g., stainless steel, platinum, nickel, nickel-titanium, etc., while distal handle hub 124 (or just the handle portion over the radiating portion of the ablation probe) may be fabricated from one of the non-conductive materials previously mentioned.

The distal ends of inflow tubing 17 and outflow tubing 19 may be positioned within handle body 112 such that fluid is pumped into handle body 112 via the pump 40 through inflow tubing 17. Fluid entering handle body 112 may come into direct contact with at least a portion of the shaft of antenna 104 to allow for convective cooling of the antenna shaft to occur. The fluid may be allowed to exit handle body 112 via inflow outflow tubing 19. In one embodiment, the outer jacket 108 may remain in direct fluid communication with inflow tubing 17 and outflow tubing 19 such that fluid contacts the antenna 104 directly along a portion of the length, or a majority of the length, or the entire length of antenna 104. Thus, the cooling assembly 100 is effective in cooling the antenna 104 directly rather than cooling the tissue surrounding the antenna 104, although the surrounding tissue may also be conductively cooled via assembly 100.

Figure 4:
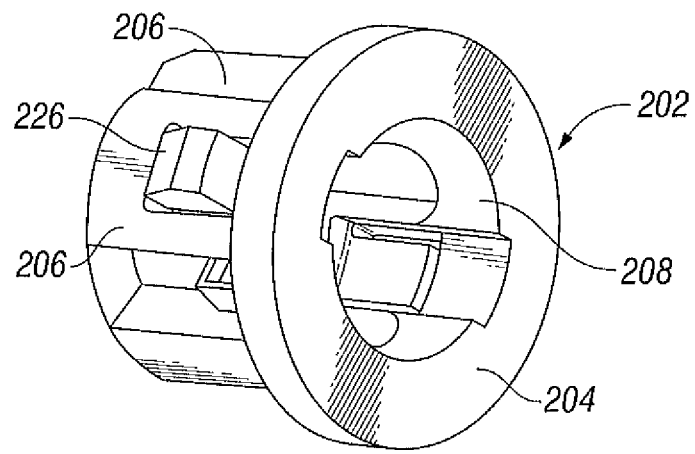
FIG. 4 is a perspective view of a wedge coupling according to one embodiment of the present disclosure.

The inflow and outflow tubing 17 and 19 are inserted into their respective nozzle adapters 200. The inflow and outflow tubing 17 and 19 are secured to the adapters 200 by a wedge coupling 202 which is shown in FIG. 4. For sake of simplicity the wedge coupling 202 is described with respect to the inflow tubing 17. During assembly, the tubing 17 is inserted into the wedge coupling 202. Thereafter the tubing 17 along with the wedge coupling 202 disposed thereon is inserted into the housing 201 over the nozzle adapter 200. Once the tubing 17 is in place, the wedge coupling 202 is pushed into the housing 201 securing the tubing 17 within the housing 201. Additional embodiments of using the wedge coupling 202 to connect multiple tubes to multiple nozzle adapters 200 on various medical instruments and equipment is within the purview of those skilled in the art.

With reference to FIGS. 4-8, the wedge coupling 202 includes a base 204, a plurality of prongs 206 extending therefrom and an opening 208 defined within the base 204 and surrounded by the prongs 206. The opening 208 has an inner diameter that is substantially equal to the outer diameter of the tubing 17 allowing the wedge coupling 202 to be slidably disposed on the tubing 17 and for the tubing 17 to pass therethrough.

Figure 5:
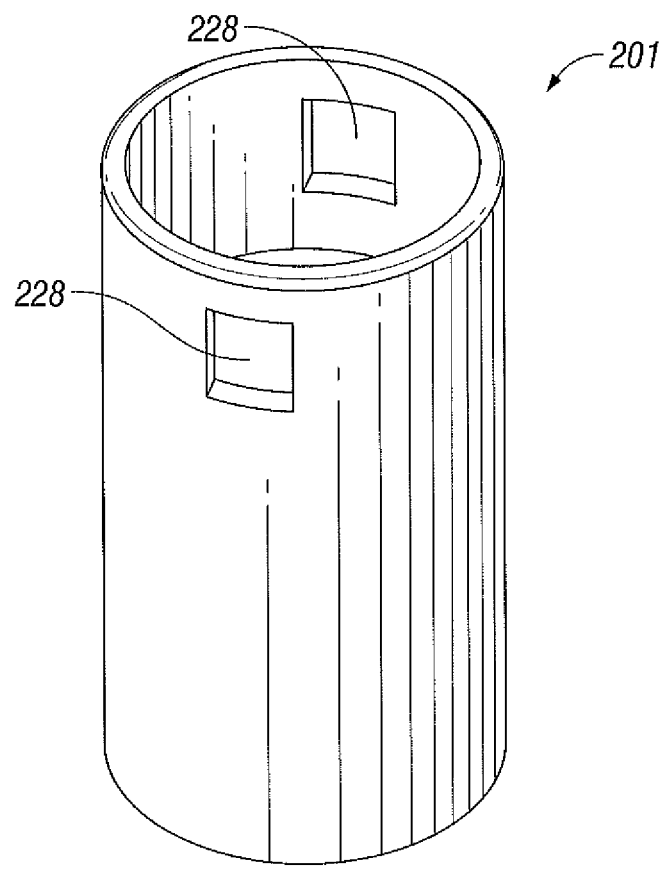
FIG. 5 is a perspective view of a housing according to one embodiment of the present disclosure.
Figure 6:
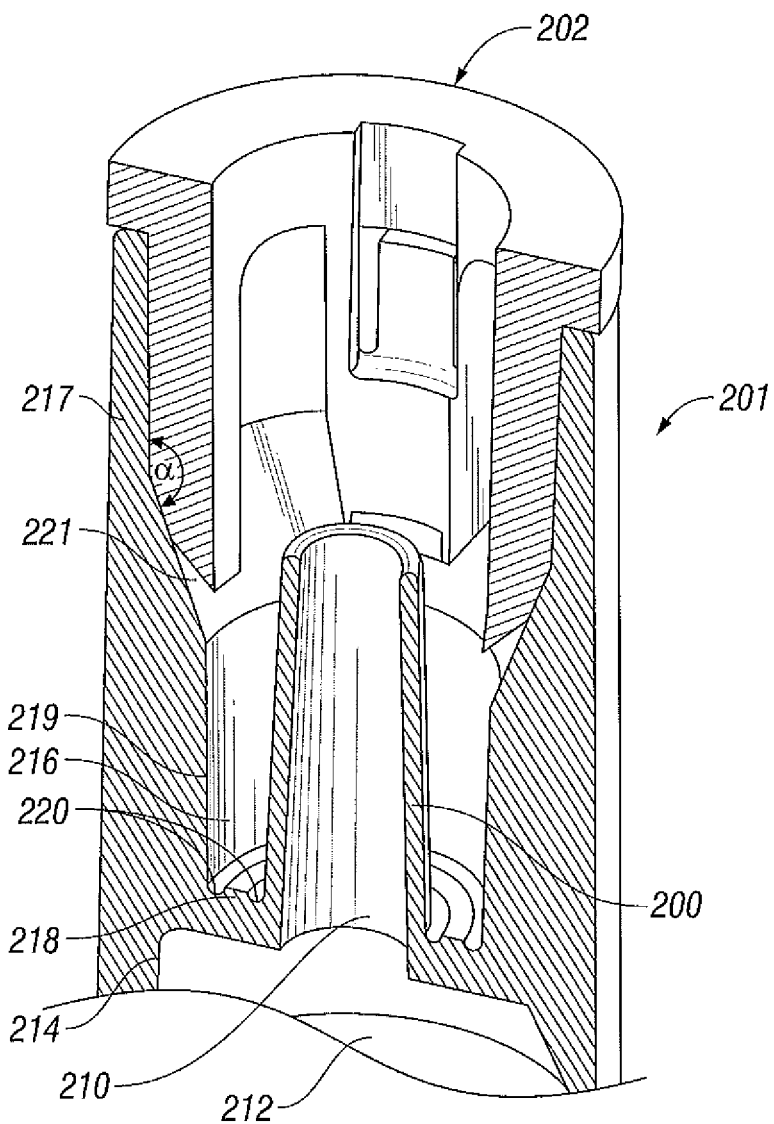
FIG. 6 is a perspective cross-sectional view of the wedge coupling and the housing according to the present disclosure.

FIGS. 5 and 6 show tube housing 201 including the nozzle adapter 200 that has an opening 210 providing access to a flow tube 212. The housing 201 also includes a funnel-shaped inner surface 216 having a proximal portion 217 and a distal portion 219 connected by a transition portion 221. The proximal portion 217 has an inner diameter larger than the diameter of the distal portion 219 with the transition portion 221 having sloping walls at a predetermined angle α providing for the transition between the portions 217 and 219.

The nozzle adapter 202 is connected to an inner surface 216 of the housing 201 via a housing base 214. The outer surface 218 of the base 214 includes troughs 220 at the point where the adapter 202 and the inner surface 216 meet the base 214. In one embodiment, when the tubing 17 is inserted into housing 201, the pressure applied to the tubing 17 by the wedge coupling 202 forces the edges of the tubing 17 at a distal end thereof to push into the base 214. This, in turn, results in the tubing 17 separating from the adapter 202. The troughs 220 provide room for the edges of the tubing 17 to spread when the tubing 17 is pushed into the housing 201 thereby relieving the pressure. This provides for a secure seal between the tubing 17 and the adapter 202.

Figure 7:
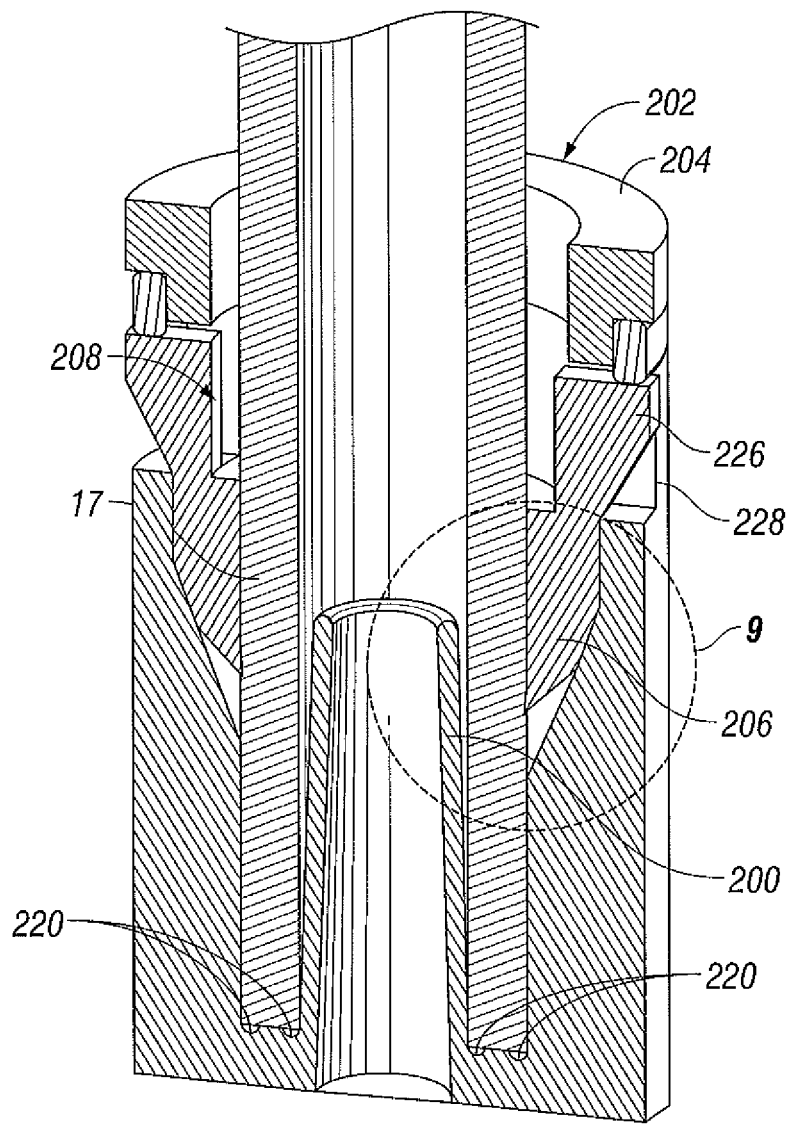
FIGS. 7 and 8 are partial cross-sectional views of the wedge coupling and the housing according to the present disclosure.
Figure 8:
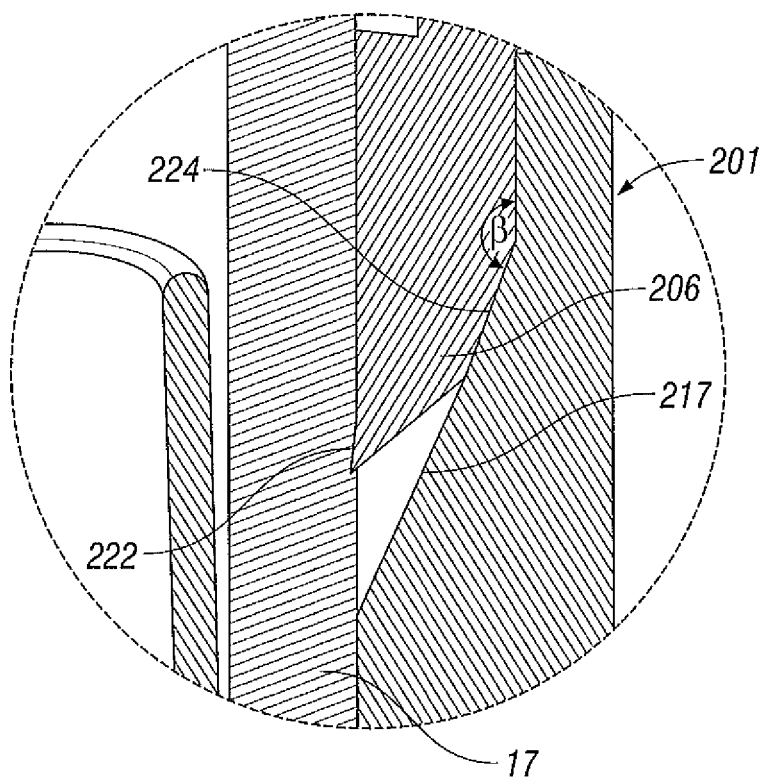

With reference to FIGS. 7 and 8, the tubing 17 being inserted within the housing 201 and being secured by the wedge coupling 202 is shown. As discussed above, the wedge coupling 202 includes two or more prongs 206 disposed on the base 204. The prongs 206 may be disposed in equiangular configuration such that when equal pressure is applied to each of the prongs 206 and the tubing 17, the forces cancel out and the tubing 17 is secured by the wedge coupling 202. The prongs 206 are configured to be slidably received within the housing 201 and to be deflected inwards thereby to secure the tubing 17 to the nozzle adapter 200.

With reference to FIG. 8, the prongs 206 include a tooth-shaped feature 222 at a distal end thereof. In addition, the prongs 206 may include a tapered portion 224 at a predetermined angle β at the distal end thereof. The angle β of the tapered portion 224 is larger than the angle α of the transitional portion 219. Thus, the prongs 206 are forced inwardly by the housing 201 as the wedge coupling 202 is inserted therein. More specifically, as the prongs 206 are inserted into the housing 201, the tapered portions 224 of the prongs 206 are in contact with the proximal portion 217. Due to the larger deflection angle of the tapered portions 224, the prongs 206 are bent inwardly against the tubing 17. The features 222 engage the outer surface of the tubing 17 and secure the tubing 17 to the nozzle adapter 200. The wedge coupling 202 may be formed from any suitable material and, in some embodiments, materials having high tensile strength allowing the prongs 206 to bend under pressure and compress the tubing 17 thereby securing the tubing 17 within the housing 201.

The wedge coupling 202 is secured to the housing 201 to prevent the wedge coupling 202 from sliding out due to the deflection of the prongs 206 by the housing 201. As shown in FIGS. 4 and 8, the wedge coupling 202 may include one or more box clips 226 that are configured to interface with corresponding windows 228 (FIG. 5). The box clips 226 may be integrally formed with and/or may be cut out within the prongs 206 allowing the prongs 206 act as a spring. The box clips 226 extend further outward than the outer surface of the prongs 206 similar to the base 204. The base 204 and the box clips 226 protrude past the proximal portion 217 of the inner surface 216. Thus, when the wedge coupling 202 is inserted into the housing 201 the base 204 rests against the proximal end of the housing 201. Similarly, the box clips 226 are compressed by the proximal portion 217 until the wedge coupling 202 is fully inserted into the housing 201. At which point, the box clips 226 are aligned with the corresponding windows 228 and the box clips 226 are deflected therein. The box clips 226 are thereafter biased against the windows 228 by the deflection of the prongs 206 and the transitional portion 219 thereby preventing the wedge coupling 202 from sliding out of the housing 201.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An assembly for use with an ablation probe, the assembly comprising:
    an inflow housing defining an inflow axis, and an outflow housing defining an outflow axis, the inflow housing and the outflow housing extending longitudinally along their respective axes in side-by-side relation and parallel orientation relative to one another, the inflow housing and the outflow housing each including:
        a funnel-shaped inner surface;
        a nozzle adapter connected to the funnel-shaped inner surface; and
        a housing base from which the nozzle adapter extends, the housing base including at least one trough defined therein;
    an inflow tubing and an outflow tubing, each tubing configured to slide into the respective funnel-shaped inner surface and over the respective nozzle; and
    an inflow wedge coupling and an outflow wedge coupling, each including:
        a base having an opening defined therein configured to receive a portion of the respective tubing therethrough; and
        a plurality of prongs disposed on the respective base around an inner periphery of the respective opening, the plurality of prongs configured to slidably engage an the respective housing and to deflect inwardly to secure the respective tubing to the respective nozzle adapter,
    wherein the at least one trough of each of the inflow housing and the outflow housing is configured to accommodate spreading of the respective tubing when the respective tubing is coupled to the respective housing.

2. The assembly according to claim 1, wherein each housing base includes a plurality of concentrically-spaced troughs defined therein.

3. The assembly according to claim 1, wherein each funnel-shaped inner surface includes a proximal portion, a distal portion, and a transitional portion having sloping walls at a first predetermined angle.

4. The assembly according to claim 3, wherein each prone of each plurality of prongs includes a tapered portion at a distal end thereof, the tapered portion having a tooth-shaped feature configured to engage the respective tubing.

5. The assembly according to claim 4, wherein the tapered portion is tapered at a second predetermined angle that is larger than the first predetermined angle thereby providing for deflection of each prong of the plurality of prongs upon insertion into the respective housing.

6. The assembly according to claim 1, further comprising:
a plurality of box clips coupled to respective ones of each of the plurality of prongs, wherein each box clip of the plurality of box clips is configured to deflect upon insertion into the respective housing and to interface with a corresponding window defined within the respective housing.

7. The assembly according to claim 1, wherein the inflow housing and the outflow housing share a common housing portion disposed between the axes thereof.

8. The assembly according to claim 7, wherein the inflow wedge coupling and the outflow wedge are each configured to contact the common housing portion upon insertion of the respective wedge coupling into the respective housing.

* * * * *